(12) United States Patent
Seifert et al.

(10) Patent No.: US 6,657,085 B2
(45) Date of Patent: Dec. 2, 2003

(54) PROCESS FOR THE PREPARATION OF ANILINE COMPOUNDS

(75) Inventors: Gottfried Seifert, Münchwilen (CH); Thomas Rapold, Münchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/276,474

(22) PCT Filed: May 15, 2001

(86) PCT No.: PCT/EP01/05529

§ 371 (c)(1),
(2), (4) Date: Nov. 15, 2002

(87) PCT Pub. No.: WO01/87806

PCT Pub. Date: Nov. 22, 2001

(65) Prior Publication Data

US 2003/0114690 A1 Jun. 19, 2003

(30) Foreign Application Priority Data

May 17, 2000 (CH) ..................... 2000 0979/00
Aug. 28, 2000 (CH) ..................... 2000 1671/00

(51) Int. Cl.$^7$ ............................. C07C 209/36
(52) U.S. Cl. ............. 564/416; 564/417; 564/418; 564/394; 564/413
(58) Field of Search ............... 564/394, 413, 564/416, 417, 418

(56) References Cited

U.S. PATENT DOCUMENTS 5,332,717 A    7/1994   Lüthy et al.

FOREIGN PATENT DOCUMENTS

| | | |
|---|---|---|
| DE | 15 18 107 | 3/1972 |
| EP | 0 416 118 | 3/1991 |
| EP | 0 481 316 | 4/1992 |
| EP | 0 895 985 | 2/1999 |
| WO | 91/05781 | 5/1991 |

OTHER PUBLICATIONS

Database CAPLUS on STN, Acc. No. 1975:31200, Trudy Instituta–Moskovskii Khimiko–Tekhnologicheskii Institut imeni D. I. Mendeleeva (1973), 74, p. 50–55 (abstract).*

Database CAPLUS on STN, Acc. No. 1991:246883, Synthetic Communications (1991), 21(2), p. 161–165 (abstract).*

An Antimalarial Alkaloid From Hydrangea. XVII. Some 5–Substituted Derivatives, B.R. Baker, et al., J. Org. Chem. 17, 164–176 (1952).

R.v.Rothenburg: Behaviour fo Hydrazine Hydrate Towards Nitro, Nitroso and Isonitroso Groups, Ber. Deutsch. Chem. Ges. 26, 2060–61 (1893).

Research Results from the Laboratory of Organic Chemistry of the Technical University of Dresden, J. Prac. Chem. 53, 433–471 (1896).

About the Influence of Hydrazine on Nitro and Chloronitro Derivatives of Benzene and Naphthalene, E. Müller, J. Prac. Chem. 111, 277–292 (1925).

* cited by examiner

*Primary Examiner*—Brian Davis
(74) *Attorney, Agent, or Firm*—Thomas Hamilton

(57) ABSTRACT

A process for the preparation of aniline compounds of formula:

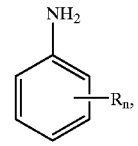

I wherein
n and R are as defined in claim 1, by reacting nitro compounds of formula:

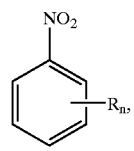

II wherein n and R are as defined, with hydrazine at elevated temperature in the presence of an aqueous base.

The compounds of formula I are suitable as intermediates in the preparation of herbicides of the isobenzofuranone type.

2 Claims, No Drawings

PROCESS FOR THE PREPARATION OF ANILINE COMPOUNDS

This application is a 371 filing of International Application No. PCT/EP01/05529, filed May 15, 2001, the contents of which are incorporated herein by reference.

The present invention relates to a new process for the preparation of aniline compounds and to their use as intermediates in the preparation of herbicides of the isobenzofuranone type.

"Berichte der deutschen chemischen Gesellschaft", 1893, page 2060, already makes mention of the reduction of nitrobenzene to aniline using hydrazine hydrate in alcoholic solution. "Journal für praktische Chemie", 1896, pages 433 to 447, discloses the use of phenylhydrazine in the reduction of nitrobenzenes to corresponding anilines. A further description of the action of hydrazine on nitro- and chloronitro-benzenes is found in "Journal für praktische Chemie", 1925, pages 277 to 284. The reactions are carried out without exception at elevated temperature, in some instances proceeding in alcoholic solution.

It has now been found, surprisingly, that the reduction of nitrobenzenes to anilines can be significantly improved if, instead of alcohol, an aqueous base is used as solvent.

The present invention accordingly relates to a process for the preparation of aniline compounds of formula:

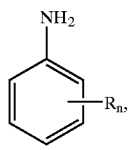

I wherein
n is an integer from 1 to 5 and
R is hydrogen, alkyl, hydroxyalkyl, alkylamino, dialkylamino, alkenyl, alkynyl, alkoxy, alkylthio, phenyl, naphthyl, phenoxy, phenylthio, halogen, amino, hydroxy, mercapto, carboxyl, sulfo, nitro, nitroso, hydroxylamino or heterocyclyl, by reacting nitro compounds of formula

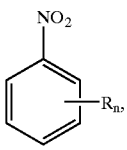

II wherein n and R are as defined, with hydrazine at elevated temperature in the presence of a solvent and isolating the compounds of formula I, in which process an aqueous base is used as solvent.

In the compounds of formula I, n is preferably an integer from 1 to 3. n is especially 2. Those compounds of formula I which have a carboxyl or sulfo group or a salt thereof have been found to be especially suitable and especially valuable. In particular, the compound of formula I which has a carboxyl group in the ortho position and a hydroxyalkyl group, especially a $CH_3CH(OH)$ group, in the meta position (3 position) has proved to be especially advantageous. The nitro compound of formula II corresponding to that compound is present in aqueous solution in a pH-dependent hydrolysis equilibrium with the corresponding closed lactone form, 3-methyl-7-nitro-3H-isobenzofuran-1-one. The latter compound, which can also be obtained, for example, by reduction of the 2-nitro-6-acetylbenzoic acid known from Horii et al., Yakugaku Zasshi, 1954, 466 and Baker et al., J. Org. Chem. 1952, 17, 164 using sodium borohydride, is new and the present invention relates also thereto. That compound too can be advantageously used in the preparation of herbicides of the isobenzofuranone type.

In general, compounds of formulae I and II that have, adjacent to one another, substituents capable of together forming a (fused-on) ring, for example a carboxyl group in the ortho position and a hydroxyalkyl group in the meta position, are present in aqueous solution in a pH-dependent equilibrium with the corresponding closed form, e.g. the lactone form, the 5-membered ring lactone form, for example in 7-amino-3-methyl-3H-isobenzofuran-1-one, being especially readily formed in acid solution. As a rule, the tendency towards ring formation decreases with increasing ring size. 6- and 7-membered rings generally form less readily than the 5-membered rings.

The process according to the invention therefore also encompasses the preparation of those closed forms of the compounds of formula I wherein two substituents R have formed a fused-on ring.

The alkyl radicals appearing in the definitions of R preferably contain from 1 to 4 carbon atoms and are, for example, methyl, ethyl, propyl and butyl and branched isomers thereof. Preferred alkoxy, alkylthio and hydroxyalkyl radicals are derived from the mentioned alkyl radicals. Alkenyl and alkynyl radicals R preferably have from 2 to 4 carbon atoms and are, for example, ethenyl, propenyl, ethynyl, propynyl and propenyl and branched isomers thereof, and butenyl and butynyl and branched and di-unsaturated isomers thereof. The terms hydroxy (—OH), mercapto (—SH) and sulfo (—SO$_3$H) and carboxyl (—CO$_2$H) also include in each case the salt form thereof, for example alkali metal, alkaline earth metal and ammonium salts. Heterocyclyl is understood to mean preferably from 4- to 8-membered, saturated or unsaturated rings that contain at least one hetero atom selected from nitrogen, sulfur and oxygen. Examples thereof are pyridyl, furanyl, thiofuranyl, oxetanyl, thiazinyl, morpholinyl, piperazinyl, pyridazinyl, pyrazinyl, thiopyranyl, pyrazolyl, pyrimidinyl, triazinyl, isofuranyl, pyranyl, piperidyl, picolinyl, thiadiazolinyl, thietanyl, triazolyl, oxazolanyl, thiolanyl, azepinyl, thiazolyl, isothiazolyl, imidazolyl or pyrrolyl.

Hydrazine may be used as such or, preferably, in the form of its hydrate. Preference is given to the use of from 1.4 to 3 mol, especially from 1.6 to 2 mol, of hydrazine compound per mol of nitro compound.

The phrase 'elevated temperature' preferably denotes a temperature range of from 30 to 150° C. It is especially preferable to proceed in a range of from 70 to 100° C., as reaction temperatures of more than 100° C. require the use of pressure.

A suitable aqueous base is especially an aqueous solution of an alkali metal hydroxide, alkaline earth metal hydroxide, alkali metal carbonate or alkaline earth metal carbonate. Organic amines, for example alkylenediamines, urotropine and quinuclidine, are also suitable. Preference is given to the use of from 0.5 to 5 mol, especially from 1 to 2 mol, of base per mol of nitro compound. If the nitro compound of formula II already contains acid groups as substituents, an additional mole of base is required for each acid group.

The process according to the invention has the major advantage that it can be carried out on a large industrial scale. The procedure is generally that the compound of formula II is introduced into water and base is added. After heating the resulting mixture to the desired reaction temperature, hydrazine or hydrazine hydrate is metered in.

The process according to the invention can be carried out either continuously or intermittently (discontinuously, batch-wise), with preference being given to intermittent operation. Both the intermittent and the continuous reaction procedures are carried out preferably in a stirred vessel or a stirred vessel cascade.

Isolation of the aniline compounds is dependent upon the structure and nature of the compound and is carried out where appropriate after acidifying the reaction mixture with, for example, hydrochloric acid to a pH in the range from 1 to 9, especially from 5 to 8, either by crystallisation or, if the product is liquid at room temperature, by extraction with an organic solvent, for example toluene.

The yields of isolated aniline compound are generally in the range from 80 to 100%. The chemical yield in the reaction mixture is usually more than 97%.

The process according to the invention has the following advantages over the process of the prior art:
it can be performed on a large industrial scale
the reaction can to a large extent be controlled by means of metered additions, which is advantageous from the aspect of safety
compared with ethanol as solvent, the reaction proceeds quickly and very selectively
when starting from compounds of formula II, especially those wherein R is sulfo or carboxyl or a corresponding salt, in the form of an aqueous solution, as may be the case, for example, in the continuous process, those compounds can be reduced directly by the addition of base together with hydrazine
it results in products in yields of up to 100%
it can be performed in a multi-purpose apparatus.

The aniline compounds of formula I prepared according to the invention are used, in particular, as intermediates in the preparation of herbicides of the isobenzofuranone type, which are described, for example, in U.S. Pat. No. 5,332,717 and U.S. Pat. No. 5,428,002.

The Examples that follow illustrate the invention further.

EXAMPLE 1
Preparation of 2-amino-6-(1-hydroxyethyl)-benzoic acid (Sodium Salt)

0.75 mol of aqueous sodium hydroxide solution (30%) are added to an aqueous solution of 0.5 mol of 2-nitro-6-(1-hydroxyethyl)-benzoic acid (sodium salt), and, at 90–95° C., 50 g of hydrazine hydrate (1.0 mol) are metered in over the course of 1 hour. Stirring is carried out at 90–95° C. for 4–6 hours until the nitro compound has been completely converted and, after isolation, 2-amino-6-(1-hydroxyethyl)-benzoic acid (sodium salt) is obtained in a yield of 97% of theory, based on 2-acetyl-6-nitrobenzoic acid (LC analysis).

EXAMPLE 2
Preparation of 2-amino-4-chlorobenzoic acid

In a stirred 1 liter Teflon vessel, 201.5 g of 4-chloro-2-nitrobenzoic acid (1 mol) are introduced into 500 ml of water, and 3 mol of aqueous sodium hydroxide solution (30%) are metered in, with stirring. The reaction mixture is heated and, at 90–95° C., 100 g of hydrazine hydrate (2 mol) are metered in over the course of 60 minutes. Stirring is carried out for 3–4 hours until the 4-chloro-2-nitrobenzoic acid has been completely converted to 2-amino-4-chlorobenzoic acid. The reaction mixture is then adjusted to a pH of 6 using hydrochloric acid (32%), the aminobenzoic acid precipitating out in crystalline form. The crystal slurry is cooled to room temperature, filtered, washed with water and dried in vacuo. 166 g of 2-amino-4-chlorobenzoic acid having a content of 99% (LC method) are obtained, which corresponds to a yield of 96% of theory, based on 4-chloro-2-nitrobenzoic acid.

EXAMPLE 3
Preparation of 7-[(4,6-dimethoxypyrimidin-2-yl)thio]-3-methyl-3H-isobenzofuran-1-one In a 2.5 liter sulfonation flask, a 50% aqueous solution of 2-amino-6-(1-hydroxyethyl)-benzoic acid (sodium salt) (1 mol) is diazotised in 3.75 mol of hydrochloric acid (32%) using 1.05 mol of sodium nitrite solution (40%) at 0–3° C. The diazo solution is then, with stirring at 50° C., metered into a mixture of 500 ml of water, 666 g of sodium hydroxide solution (30%) (5 mol) and 176 g of potassium ethyl xanthogenate (1.1 mol) over the course of 60 minutes. At 50° C., the reaction mixture is adjusted to a pH of 3 using hydrochloric acid 32%; the intermediate 7-mercapto-3-methyl-3H-isobenzofuran-1-one separates out in the form of an oil and is separated off from the aqueous phase. The intermediate is metered, at 70° C., into a mixture of 1.0 mol of 2-chloro-4,6-dimethoxy-pyrimidine and 1.05 mol of potassium carbonate in 1600 ml of acetonitrile and is stirred for 4–6 hours until the conversion is complete. 700 ml of water are added to the reaction mixture and the aqueous salt solution is separated off from the organic phase, which contains 7-[(4,6-dimethoxypyrimidin-2-yl)thio]-3-methyl-phthalide. 700 ml of water are added to the organic phase and cooling to room temperature is carried out; 7-[(4,6-dimethoxypyrimidin-2-yl)thiol]-3-methyl-3H-isobenzofuran-1-one precipitates out in crystalline form, is filtered off and is washed with 300 ml of isopropanol. After drying in vacuo at 70° C., 7-[(4,6-dimethoxypyrimidin-2-yl)thiol]-3-methyl-3H-isovenzofuran-1-one is obtained in a yield of 70% of theory (based on 2-amino-6-(1-hydroxyethyl)-benzoic acid sodium salt) in a purity of 98% (LC method).

EXAMPLE 4
Preparation of 3-methyl-7-nitro-3H-isobenzofuran-1-one 10.0 g (48 mmol) of 2-nitro-6-acetyl-benzoic acid (cf. Horii et al., Yakugaku Zasshi, 1954, 466, and Baker et al., J. Org. Chem. 1952, 17, 164) are dissolved at 40° C. in 50 ml of 2N sodium hydroxide solution and treated with 1.87 g (48 mmol) of sodium borohydride in portions. After 40 minutes, the reaction mixture, which has been cooled, is acidified and the precipitated crystals are filtered off and dried in vacuo; the product consists of 8.4 g of a product mixture of 82% of 2-nitro-6-(1-hydroxyethyl)-benzoic acid; $^1$H-NMR (DMSO-$D_6$): 8.00 ppm, m, 2H; 7.68 ppm, t, 1H; 5.6 ppm, b, OH; 4.92 ppm, q, 1H; 1.32 ppm, d, 3H; and 18% of 3-methyl-7-nitro-3H-isobenzofuran-1-one; $^1$H-NMR (DMSO-$D_6$): 8.02 ppm, m, 2H; 7.68 ppm, t, 1H; 5.80 ppm, q, 1H; 1.62 ppm, d, 3H. The acid aqueous phase is then also extracted with ethyl acetate, combined with the crystals obtained above, dried thoroughly over magnesium sulfate and concentrated completely to dryness by evaporation. 9.14 g (98.6%) of pure 3-methyl-7-nitro-phthalide (3-methyl-7-nitro-3H-isobenzofuran-1-one) are thereby obtained; $^1$H-NMR ($CDCl_3$): 7.92 ppm, d, 1H; 7.88 ppm, t, 1H; 7.72 ppm, d, 1H; 5.63 ppm, q, 1H; 1.72 ppm, d, 3H.

EXAMPLE 5
Preparation of 7-amino-3-methyl-3H-isobenzofuran-1-one 2.37 g (12.2 mmol) of 3-methyl-7-nitro-3H-isobenzofuran-1-one (Example 4) are heated in 5 ml of 30% sodium hydroxide solution (49 mmol) for 1 hour at 90° C.

until 2-nitro-6-(1-hydroxyethyl)-benzoic acid can be demonstrated almost quantitatively by TLC (mobile phase: ethyl acetate/hexane 3:1 plus 1 drop of formic acid). 1.2 ml (24.5 mmol) of hydrazine hydrate are then slowly added dropwise and the temperature is maintained for a further 4 hours. The cooled reaction mixture is then adjusted to a pH of 2 and is extracted with ethyl acetate. 1.8 g (90.4%) of crude 7-amino-3-methyl-3H-isobenzofuran-1-one are obtained; $^1$H-NMR (CDCl$_3$): 7.37 ppm, t, 1H; 6.63 ppm, d, 1H; 6.61 ppm, d, 1H; 5.44 ppm, q, 1H; 5.22 ppm, b, 2H; 1.58 ppm, d, 3H.

What is claimed is:

1. A process for the preparation of an aniline compound of formula:

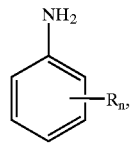

I wherein
n is an integer from 1 to 5 and
R is hydrogen, alkyl, hydroxyalkyl, alkylamino, dialkylamino, alkenyl, alkynyl, alkoxy, alkylthio, phenyl, naphthyl, phenoxy, phenylthio, halogen, amino, hydroxy, mercapto, carboxyl, sulfo, nitro, nitroso, hydroxylamino or heterocyclyl, by reacting a nitro compound of formula:

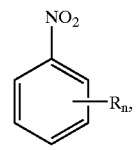

II wherein n and R are as defined, with hydrazine at elevated temperature in the presence of a solvent, in which process an aqueous base is used as solvent.

2. The compound 3-methyl-7-nitro-3H-isobenzofuran-1-one.

* * * * *